US009629855B2

(12) United States Patent
Lee et al.

(10) Patent No.: US 9,629,855 B2
(45) Date of Patent: Apr. 25, 2017

(54) PHARMACEUTICAL COMPOSITION FOR TREATMENT OF EYE PAIN, CONTAINING PGE2 SYNTHESIS INHIBITOR (71) Applicant: INDUSTRY-ACADEMIC COOPERATION FOUNDATION, YONSEI UNIVERSITY, Seoul (KR)

(72) Inventors: Hyung Keun Lee, Seoul (KR); Jong Woo Shim, Seoul (KR)

(73) Assignee: INDUSTRY-ACADEMIC COOPERATION FOUNDATION, YONSEI UNIVERSITY (KR)

( * ) Notice: Subject to any disclaimer, the term of this patent is extended or adjusted under 35 U.S.C. 154(b) by 40 days.

(21) Appl. No.: 14/648,970

(22) PCT Filed: Dec. 27, 2012

(86) PCT No.: PCT/KR2012/011631
§ 371 (c)(1),
(2) Date: Jun. 2, 2015

(87) PCT Pub. No.: WO2013/100660
PCT Pub. Date: Jul. 4, 2013

(65) Prior Publication Data
US 2016/0000809 A1 Jan. 7, 2016

(30) Foreign Application Priority Data

Dec. 29, 2011 (KR) .................. 10-2011-0146450
Jul. 6, 2012 (KR) .................. 10-2012-0074204

(51) Int. Cl.
| | | |
|---|---|---|
| *A61K 38/00* | (2006.01) | |
| *A61P 9/10* | (2006.01) | |
| *A61P 27/02* | (2006.01) | |
| *A61K 31/635* | (2006.01) | |
| *A61K 9/00* | (2006.01) | |
| *A61K 31/557* | (2006.01) | |
| *A61K 31/192* | (2006.01) | |
| *A61K 31/18* | (2006.01) | |
| *A61K 38/06* | (2006.01) | |
| *A61K 31/405* | (2006.01) | |
| *A61K 31/4184* | (2006.01) | |
| *A61K 31/407* | (2006.01) | |
| *A61K 31/5415* | (2006.01) | |
| *A61K 31/015* | (2006.01) | |
| *A61K 31/425* | (2006.01) | |
| *A61K 31/00* | (2006.01) | |

(52) U.S. Cl.
CPC .......... *A61K 31/635* (2013.01); *A61K 9/0048* (2013.01); *A61K 31/00* (2013.01); *A61K 31/015* (2013.01); *A61K 31/18* (2013.01); *A61K 31/192* (2013.01); *A61K 31/405* (2013.01); *A61K 31/407* (2013.01); *A61K 31/4184* (2013.01); *A61K 31/425* (2013.01); *A61K 31/5415* (2013.01); *A61K 31/557* (2013.01); *A61K 38/06* (2013.01)

(58) Field of Classification Search
CPC ...... A61K 31/00; A61K 31/015; A61K 31/18; A61K 31/192; A61K 31/405; A61K 31/407; A61K 31/4184; A61K 31/425; A61K 31/5415; A61K 31/557; A61K 31/635; A61K 38/06; A61K 9/0048
See application file for complete search history.

(56) References Cited

U.S. PATENT DOCUMENTS

| | | | |
|---|---|---|---|
| 2002/0086070 A1 | 7/2002 | Kuhrts | |
| 2002/0128267 A1* | 9/2002 | Bandyopadhyay | .. A61K 9/0048 514/247 |
| 2010/0003354 A1* | 1/2010 | Mastrodonato | ...... A61K 9/0048 424/768 |
| 2011/0281882 A1 | 11/2011 | Zhang et al. | |

FOREIGN PATENT DOCUMENTS

WO    WO2008/016095    *    2/2008    ............. A61K 45/00

OTHER PUBLICATIONS

Carr, Managing Eye Pain. The role of over-the-counter and prescription analgesics in treating patients with ocular pain. Therapeutic Insights. Optometric Management, Issue: Aug. 2001. http://www.optometricmanagement.com/printarticle.aspx?articleID=70232, accessed online May 23, 2016. 5 pages.*
El-Shazly et al. Comparison between two cyclooxygenase inhibitors in an experimental dry eye model in albino rabbits. Acta Pharm. vol. 58. 2008, pp. 163-173.*
Arthritis Foundation. Sjogren's syndrome. Accessed online at: https://static.medicine.iupui.edu/divisions/rheu/content/patienthandouts/Sjogrens_brochure.pdf on Sep. 10, 2016. 2002, pp. 1-6.*
Celecoxib: An NSAID with Improved Gastrointesinal Tolerability. Drug Ther Perspect. 2001, vol. 17, No. 5, Accessed online at http://www.medscape.com/viewarticle/406471_print, pp. 1-6.*

(Continued)

*Primary Examiner* — Marcela M Cordero Garcia
(74) *Attorney, Agent, or Firm* — Sheridan Ross P.C.

(57) ABSTRACT

The present invention relates to a pharmaceutical composition for the treatment of eye pain, containing a PGE2 synthesis inhibitor. The use of the pharmaceutical composition for the prevention or treatment of eye pain according to the present invention, which contains the PGE2 synthesis inhibitor as an active ingredient, makes it possible to alleviate the symptoms of eye pain by selectively inhibiting the PGE2 expression level, and also has the advantages of treating and preventing xerophthalmia and of overcoming and preventing eye discomfort caused by various inflammation-inducing circumstances including following surgery. Also, by using a kit for detecting the amount of PGE2, PGD2 and COX2, the present invention makes it possible to easily diagnose eye-pain symptoms in clinical practice, and can be widely used in checking the state not only of patients having xerophthalmia but also patients following eye surgery.

2 Claims, 4 Drawing Sheets (56) References Cited

OTHER PUBLICATIONS

Karpecki et al. Systemic Disease and Dry Eye, Published Sep. 19, 2010. Accessed online at https://www.reviewofoptometry.com/article/systemic-disease-and-dry-eye on Sep. 10, 2016, 16 pages.*
Furst. Meloxicam: Selective COX-2 Inhibition in Clinical Practice. Semin Arthritis Rheum, 1997. vol. 26, pp. 21-27.*
Barner. Review of Clinical Trials and Benefit/Risk Ratio of Meloxicam. Scand J Rheumatol, 1996. vol. 25 (Suppl 102), pp. 29-37.*
WO2008016095, published Feb. 2008, Machine translation to English, 20 pages.*
International Search Report prepared by the Korean Intellectual Property Office on Jun. 27, 2013, for International Application No. PCT/KR2012/011631.
Written Opinion prepared by the Korean Intellectual Property Office on Jun. 27, 2013, for International Application No. PCT/KR2012/011631.
International Preliminary Report on Patentability prepared by the Korean Intellectual Property Office on Jul. 1, 2014, for International Application No. PCT/KR2012/011631.
Kulkarni, P.S. et al. "The effect of intravitreal and topical prostaglandins on intraocular inflammation." Invest, Ophthamol. Vis. Sci., 1982, vol. 23, No. 3, pp. 382-392; See pp. 383 and 385.
Bhattacherjee, P. et al. "Inhibition of the prostaglandin synthetase systems in ocular tissues by indomethacin." Br. J. Pharmac., 1974, vol. 50, pp. 227-230. See p. 227.
Cho, Hyung et al. "Management of ocular inflammation and pain following cataract surgery: focus on bromfenac ophthalmic solution." Clinical Ophthalmology, 2009, vol. 3, pp. 199-210. See p. 199.
Chen et al. "sPLA2-IIa is an inflammatory mediator when the ocular surface is compromised," Experimental Eye Research, May 2009, vol. 88, No. 5, pp. 880-888.
Frucht et al. "Topical indomethacin effect on neovascularisation of the cornea and on prostaglandin E2 levels," British Journal of Opthalmology, 1984, vol. 68, No. 9, pp. 656-659.
Guerrero et al. "Synthesis and Pharmacological Evaluation of a Selected Library of New Potential Anti-inflammatory Agents Bearing the y-Hydroxybutenolide Scaffold: a New Class of Inhibitors of Prostanoid Production through the Selective Modulation of Microsomal Prostaglandin E Synthase-1 Expression," Journal of Medicinal Chemistry, 2007, vol. 50, No. 9, pp. 2176-2184.

Kawamura et al. "Expression of Microsomal Prostaglandin E Synthase-1 in Fibroblasts of Rabbit Alkali-Burned Corneas," Cornea, Dec. 2008, vol. 27, No. 10, pp. 1156-1163.
Kubota et al. "Prevention of Ocular Inflammation in Endotoxin-Induced Uveitis with Resveratrol by Inhibiting Oxidative Damage and Nuclear Factor-kB Activation," Invetstigative Opthalmology & Visual Sciences, Jul. 2009, Vol. 50, No. 7, pp. 3512-3519.
Liclican et al. "Selective Activation of the Prostaglandin E2 Circuit in Chronic Injury-Induced Pathologic Angiogenesis," Investigative Ophthalmology & Visual Science, Dec. 2010, vol. 51, No. 12, pp. 6311-6320.
Ottino et al. "Corneal stimulation of MMP-1, -9 and uPa by platelet-activating factor is mediated by cyclooxygenase-2 metabolites," Current Eye Research, 2001, vol. 23, No. 2, pp. 77-85.
Riendeau et al. "Inhibitors of the inducible microsomal prostaglandin E2 synthase (mPGES-1) derived from MK-886," Bioorganic & Medicinal Chemistry Letters, 2005, vol. 15, No. 14, pp. 3352-3355.
Roat "Corneal Ulcer," MSD Manual, last revised Sep. 2014, 7 pages [merckmanual.jp/mmpej/sec09/ch102/ch102c.html] (with English Translation).
Roat et al. "Keratomalacia," MSD Manual, last revised Sep. 2014, 3 pages [merckmanula.jp/mmpej/sec09/ch102/ch102g.html] (with English Translation).
Salo et al. "A Randomized, Clinical Trial Comparing Oral Celecoxib 200mg, Celecoxib 400mg, and Ibuprofen 600mg for Acute Pain," Academic Emergency Medicine, Jan. 2003, vol. 10, No. 1, pp. 22-30.
Stanke-Labesque et al. "Inhibition of leukotriene synthesis with MK-886 prevents a rise in blood pressure and reduces noradrenaline-evoked contraction in L-NAME-treated rats," British Journal of Pharmacology, 2003, vol. 140, pp. 186-194.
Taylor et al. "Sulindac Sulfone Inhibits k-ras-dependent Cyclooxygenase-2 Expression in Human Colon Cancer Cells," Cancer Research, 2001, vol. 60, No. 23, pp. 6607-6610.
Xu et al. "MF63-2-(6-Chloro-1H-phenanthro[9, 10-d]imidazol-2-yl)-isophthalonitrile], a Selective Microsomal Prostaglandin E Synthase-1 Inhibitor, Relieves Pyresis and Pain in Preclinical Models of Inflamation," Journal of Pharmacology and Experimental Therapeutics, 2008, vol. 326, No. 3, pp. 754-763.
Yamada et al. "The effect of selective cyclooxygenase-2 inhibitor on corneal angiogenesis in the rat," Current Eye Research, 1999, vol. 19, No. 4, pp. 300-304.
Official Action for Japan Patent Application No. 2014-550020, dated Jun. 23, 2015, 8 pages.
Official Action for Japan Patent Application No. 2014-550020, dated Nov. 10, 2015, 4 pages.

* cited by examiner

```
SEQUENCE LISTING

<160> NUMBER OF SEQ ID NOS: 4

<210> SEQ ID NO 1
<211> LENGTH: 377
<212> TYPE: PRT
<213> ORGANISM: Homo sapiens

<400> SEQUENCE: 1

Met Asp Pro Ala Ala Arg Val Val Arg Ala Leu Trp Pro Gly Gly Cys
1               5                   10                  15

Ala Leu Ala Trp Arg Leu Gly Gly Arg Pro Gln Pro Leu Leu Pro Thr
            20                  25                  30

Gln Ser Arg Ala Gly Phe Ala Gly Ala Ala Gly Gly Pro Ser Pro Val
        35                  40                  45

Ala Ala Ala Arg Lys Gly Ser Pro Arg Leu Leu Gly Ala Ala Ala Leu
    50                  55                  60
```

```
Ala Leu Gly Gly Ala Leu Gly Leu Tyr His Thr Ala Arg Trp His Leu
 65                  70                  75                  80

Arg Ala Gln Asp Leu His Ala Glu Arg Ser Ala Gln Leu Ser Leu
                 85                  90                  95

Ser Ser Arg Leu Gln Leu Thr Leu Tyr Gln Tyr Lys Thr Cys Pro Phe
            100                 105                 110

Cys Ser Lys Val Arg Ala Phe Leu Asp Phe His Ala Leu Pro Tyr Gln
            115                 120                 125

Val Val Glu Val Asn Pro Val Arg Arg Ala Glu Ile Lys Phe Ser Ser
130                 135                 140

Tyr Arg Lys Val Pro Ile Leu Val Ala Gln Glu Gly Glu Ser Ser Gln
145                 150                 155                 160

Gln Leu Asn Asp Ser Ser Val Ile Ile Ser Ala Leu Lys Thr Tyr Leu
                165                 170                 175

Val Ser Gly Gln Pro Leu Glu Glu Ile Ile Thr Tyr Tyr Pro Ala Met
            180                 185                 190

Lys Ala Val Asn Glu Gln Gly Lys Glu Val Thr Glu Phe Gly Asn Lys
            195                 200                 205

Tyr Trp Leu Met Leu Asn Glu Lys Glu Ala Gln Gln Val Tyr Gly Gly
210                 215                 220

Lys Glu Ala Arg Thr Glu Glu Met Lys Trp Arg Gln Trp Ala Asp Asp
225                 230                 235                 240

Trp Leu Val His Leu Ile Ser Pro Asn Val Tyr Arg Thr Pro Thr Glu
                245                 250                 255

Ala Leu Ala Ser Phe Asp Tyr Ile Val Arg Glu Gly Lys Phe Gly Ala
            260                 265                 270

Val Glu Gly Ala Val Ala Lys Tyr Met Gly Ala Ala Met Tyr Leu
            275                 280                 285

Ile Ser Lys Arg Leu Lys Ser Arg His Arg Leu Gln Asp Asn Val Arg
290                 295                 300

Glu Asp Leu Tyr Glu Ala Ala Asp Lys Trp Val Ala Val Gly Lys
305                 310                 315                 320

Asp Arg Pro Phe Met Gly Gly Gln Lys Pro Asn Leu Ala Asp Leu Ala
                325                 330                 335

Val Tyr Gly Val Leu Arg Val Met Glu Gly Leu Asp Ala Phe Asp Asp
            340                 345                 350

Leu Met Gln His Thr His Ile Gln Pro Trp Tyr Leu Arg Val Glu Arg
            355                 360                 365

Ala Ile Thr Glu Ala Ser Pro Ala His
370                 375

<210> SEQ ID NO 2
<211> LENGTH: 1134
<212> TYPE: DNA
<213> ORGANISM: Homo sapiens

<400> SEQUENCE: 2
atggacccgg ctgcgcgggt ggtgcgggcg ctgtggcctg gtgggtgcgc cttggcctgg      60
aggctgggag ccgcccccca gccgctgcta cccacgcaga gccgggctgg cttcgcgggg     120
gcggcgggcg gcccgagccc cgtggctgca gctcgtaagg ggagcccgcg gctgctggga     180
gctgcggcgc tggccctggg gggagccctg ggctgtacc acacggcgcg gtggcacctg     240
cgcgcccagg acctccacgc agagcgctca gccgcgcagc tctcccctgtc cagccgcctg     300 cagctgaccc tgtaccagta caagacgtgt cccttctgca gcaaggtccg agccttcctc     360
```

```
gacttccatg ccctgcccta ccaggtggtg gaggtgaacc ctgtgcgcag ggctgagatc    420
aagttctcct cctacagaaa ggtgcccatc ctggtggccc aggaaggaga aagctcgcaa    480
caactaaatg actcctctgt catcatcagc ccctcaaga  cctacctggt gtcggggcag    540
cccctggaag agatcatcac ctactaccca gccatgaagg ctgtgaacga gcagggcaag    600
gaggtgaccg agttcggcaa taagtactgg ctcatgctca acgagaagga ggcccagcaa    660
gtgtatggtg ggaaggaggc caggacggag gagatgaagt ggcggcagtg gcggacgac     720 tggctggtgc acctgatctc ccccaatgtg taccgcacgc ccaccgaggc tctggcgtcc    780
tttgactaca ttgtccgcga gggcaagttc ggagccgtgg agggtgccgt ggccaagtac    840
atgggtgcag cggccatgta cctcatcagc aagcgactca gagcaggca  ccgcctccag    900 gacaacgtgc gcgaggacct ctatgaggct gctgacaagt gggtggctgc tgtgggcaag    960
gaccggccct tcatggggggg ccagaagccg aatctcgctg atttggcggt gtatggcgtg   1020
ctgcgtgtga tggaggggct ggatgcattc gatgacctga tgcagcacac gcacatccag    1080
ccctggtacc tgcgggtgga gagggccatc accgaggcct ccccagcgca ctga          1134
```

<210> SEQ ID NO 3
<211> LENGTH: 604
<212> TYPE: PRT
<213> ORGANISM: Homo sapiens

<400> SEQUENCE: 3

```
Met Leu Ala Arg Ala Leu Leu Cys Ala Val Leu Ala Leu Ser His
1               5                   10                  15

Thr Ala Asn Pro Cys Cys Ser His Pro Cys Gln Asn Arg Gly Val Cys
            20                  25                  30

Met Ser Val Gly Phe Asp Gln Tyr Lys Cys Asp Cys Thr Arg Thr Gly
        35                  40                  45

Phe Tyr Gly Glu Asn Cys Ser Thr Pro Glu Phe Leu Thr Arg Ile Lys
    50                  55                  60

Leu Phe Leu Lys Pro Thr Pro Asn Thr Val His Tyr Ile Leu Thr His
65                  70                  75                  80

Phe Lys Gly Phe Trp Asn Val Val Asn Asn Ile Pro Phe Leu Arg Asn
                85                  90                  95

Ala Ile Met Ser Tyr Val Leu Thr Ser Arg Ser His Leu Ile Asp Ser
            100                 105                 110

Pro Pro Thr Tyr Asn Ala Asp Tyr Gly Tyr Lys Ser Trp Glu Ala Phe
        115                 120                 125

Ser Asn Leu Ser Tyr Tyr Thr Arg Ala Leu Pro Pro Val Pro Asp Asp
    130                 135                 140

Cys Pro Thr Pro Leu Gly Val Lys Gly Lys Lys Gln Leu Pro Asp Ser
145                 150                 155                 160

Asn Glu Ile Val Glu Lys Leu Leu Arg Arg Lys Phe Ile Pro Asp
                165                 170                 175

Pro Gln Gly Ser Asn Met Met Phe Ala Phe Phe Ala Gln His Phe Thr
            180                 185                 190

His Gln Phe Phe Lys Thr Asp His Lys Arg Gly Pro Ala Phe Thr Asn
        195                 200                 205

Gly Leu Gly His Gly Val Asp Leu Asn His Ile Tyr Gly Glu Thr Leu
    210                 215                 220

Ala Arg Gln Arg Lys Leu Arg Leu Phe Lys Asp Gly Lys Met Lys Tyr
225                 230                 235                 240
```

Gln Ile Ile Asp Gly Glu Met Tyr Pro Pro Thr Val Lys Asp Thr Gln
                245                 250                 255

Ala Glu Met Ile Tyr Pro Pro Gln Val Pro Glu His Leu Arg Phe Ala
            260                 265                 270

Val Gly Gln Glu Val Phe Gly Leu Val Pro Gly Leu Met Met Tyr Ala
        275                 280                 285

Thr Ile Trp Leu Arg Glu His Asn Arg Val Cys Asp Val Leu Lys Gln
    290                 295                 300

Glu His Pro Glu Trp Gly Asp Glu Gln Leu Phe Gln Thr Ser Arg Leu
305                 310                 315                 320

Ile Leu Ile Gly Glu Thr Ile Lys Ile Val Ile Glu Asp Tyr Val Gln
                325                 330                 335

His Leu Ser Gly Tyr His Phe Lys Leu Lys Phe Asp Pro Glu Leu Leu
            340                 345                 350

Phe Asn Lys Gln Phe Gln Tyr Gln Asn Arg Ile Ala Ala Glu Phe Asn
        355                 360                 365

Thr Leu Tyr His Trp His Pro Leu Leu Pro Asp Thr Phe Gln Ile His
    370                 375                 380

Asp Gln Lys Tyr Asn Tyr Gln Gln Phe Ile Tyr Asn Asn Ser Ile Leu
385                 390                 395                 400

Leu Glu His Gly Ile Thr Gln Phe Val Glu Ser Phe Thr Arg Gln Ile
                405                 410                 415

Ala Gly Arg Val Ala Gly Gly Arg Asn Val Pro Pro Ala Val Gln Lys
            420                 425                 430

Val Ser Gln Ala Ser Ile Asp Gln Ser Arg Gln Met Lys Tyr Gln Ser
        435                 440                 445

Phe Asn Glu Tyr Arg Lys Arg Phe Met Leu Lys Pro Tyr Glu Ser Phe
    450                 455                 460

Glu Glu Leu Thr Gly Glu Lys Glu Met Ser Ala Glu Leu Glu Ala Leu
465                 470                 475                 480

Tyr Gly Asp Ile Asp Ala Val Glu Leu Tyr Pro Ala Leu Leu Val Glu
                485                 490                 495

Lys Pro Arg Pro Asp Ala Ile Phe Gly Glu Thr Met Val Glu Val Gly
            500                 505                 510

Ala Pro Phe Ser Leu Lys Gly Leu Met Gly Asn Val Ile Cys Ser Pro
        515                 520                 525

Ala Tyr Trp Lys Pro Ser Thr Phe Gly Gly Glu Val Gly Phe Gln Ile
    530                 535                 540

Ile Asn Thr Ala Ser Ile Gln Ser Leu Ile Cys Asn Asn Val Lys Gly
545                 550                 555                 560

Cys Pro Phe Thr Ser Phe Ser Val Pro Asp Pro Glu Leu Ile Lys Thr
                565                 570                 575

Val Thr Ile Asn Ala Ser Ser Ser Arg Ser Gly Leu Asp Asp Ile Asn
            580                 585                 590

Pro Thr Val Leu Leu Lys Glu Arg Ser Thr Glu Leu
        595                 600

<210> SEQ ID NO 4
<211> LENGTH: 4507
<212> TYPE: DNA
<213> ORGANISM: Homo sapiens

```
<400> SEQUENCE: 4
gaccaattgt catacgactt gcagtgagcg tcaggagcac gtccaggaac tcctcagcag      60
cgcctccttc agctccacag ccagacgccc tcagacagca aagcctaccc ccgcgccgcg     120
ccctgcccgc cgctgcgatg ctcgcccgcg ccctgctgct gtgcgcggtc ctggcgctca     180
gccatacagc aaatccttgc tgttcccacc catgtcaaaa ccgaggtgta tgtatgagtg     240
tgggatttga ccagtataag tgcgattgta cccggacagg attctatgga gaaaactgct     300
caacaccgga attttgaca agaataaaat tatttctgaa acccactcca acacagtgc       360
actacatact tacccacttc aagggatttt ggaacgttgt gaataacatt cccttccttc     420
gaaatgcaat tatgagttat gtgttgacat ccagatcaca tttgattgac agtccaccaa     480
cttacaatgc tgactatggc tacaaaagct gggaagcctt ctctaacctc tcctattata     540
ctagagccct tcctcctgtg cctgatgatt gcccgactcc cttgggtgtc aaaggtaaaa     600
agcagcttcc tgattcaaat gagattgtgg aaaaattgct tctaagaaga aagttcatcc     660
ctgatcccca gggctcaaac atgatgtttg cattctttgc ccagcacttc acgcatcagt     720
ttttcaagac agatcataag cgagggccag cttccaccaa cgggctgggc catggggtgg     780
acttaaatca tatttacggt gaaactctgg ctagacagcg taaactgcgc cttttcaagg     840
atggaaaaat gaaatatcag ataattgatg gagagatgta tcctcccaca gtcaaagata     900
ctcaggcaga tgatctctac cctcctcaag tccctgagca tctacggttt gctgtggggc     960
aggaggtctt tggtctggtg cctggtctga tgatgtatgc cacaatctgg ctgcgggaac    1020
acaacagagt atgcgatgtg cttaaacagg agcatcctga tggggtgat gagcagttgt     1080
tccagacaag caggctaata ctgataggag agactattaa gattgtgatt gaagattatg    1140
tgcaacactt gagtggctat cacttcaaac tgaaatttga cccagaacta cttttcaaca    1200
aacaattcca gtaccaaaat cgtattgctg ctgaatttaa caccctctat cactggcatc    1260
cccttctgcc tgacaccttt caaattcatg accagaaata caactatcaa cagtttatct    1320
acaacaactc tatattgctg gaacatggaa ttacccagtt tgttgaatca ttcaccaggc    1380
aaattgctgg cagggttgct ggtggtagga atgttccacc cgcagtacag aaagtatcac    1440
aggcttccat tgaccagagc aggcagatga ataccagtc ttttaatgag taccgcaaac     1500
gctttatgct gaagccctat gaatcatttg aagaacttac aggagaaaag gaaatgtctg    1560
cagagttgga agcactctat ggtgacatcg atgctgtgga gctgtatcct gcccttctgg    1620
tagaaaagcc tcggccagat gccatctttg gtgaaaccat ggtagaagtt ggagcaccat    1680
tctccttgaa aggacttatg ggtaatgtta tatgttctcc tgcctactgg aagccaagca    1740
cttttggtgg agaagtgggt tttcaaatca tcaacactgc tcaattcag tctctcatct     1800
gcaataacgt gaagggctgt cccttactt cattcagtgt tccagatcca gagctcatta    1860
aaacagtcac catcaatgca agttcttccc gctccggact agatgatatc aatcccacag    1920
tactactaaa agaacgttcg actgaactgt agaagtctaa tgatcatatt tatttattta    1980
tatgaaccat gtctattaat ttaattattt aataatattt atattaaact ccttatgtta    2040
cttaacatct tctgtaacag aagtcagtac tcctgttgcg gagaaaggag tcatacttgt    2100
gaagactttt atgtcactac tctaaagatt ttgctgttgc tgttaagttt ggaaaacagt    2160
ttttattctg ttttataaac cagagagaaa tgagttttga cgtcttttta cttgaatttc    2220
aacttatatt ataagaacga aagtaaagat gtttgaatac ttaaacactg tcacaagatg    2280
gcaaaatgct gaaagttttt acactgtcga tgtttccaat gcatcttcca tgatgcatta    2340
```

-continued

```
gaagtaacta atgtttgaaa tttaaagta cttttggtta tttttctgtc atcaaacaaa      2400
aacaggtatc agtgcattat taaatgaata tttaaattag acattaccag taatttcatg      2460 tctactttt  aaaatcagca atgaaacaat aatttgaaat ttctaaattc atagggtaga      2520
atcacctgta aaagcttgtt tgatttctta aagttattaa acttgtacat ataccaaaaa      2580
gaagctgtct tggatttaaa tctgtaaaat cagtagaaat tttactacaa ttgcttgtta      2640
aaatatttta taagtgatgt tcctttttca ccaagagtat aaacctttt  agtgtgactg      2700 ttaaaacttc cttttaaatc aaaatgccaa atttattaag gtggtggagc cactgcagtg      2760
ttatcttaaa ataagaatat tttgttgaga tattccagaa tttgtttata tggctggtaa      2820
catgtaaaat ctatatcagc aaaagggtct acctttaaaa taagcaataa caaagaagaa      2880
aaccaaatta ttgttcaaat ttaggtttaa acttttgaag caaactttt  tttatccttg      2940 tgcactgcag gcctggtact cagattttgc tatgaggtta atgaagtacc aagctgtgct      3000
tgaataatga tatgttttct cagattttct gttgtacagt ttaatttagc agtccatatc      3060
acattgcaaa agtagcaatg acctcataaa atacctcttc aaaatgctta aattcatttc      3120
acacattaat tttatctcag tcttgaagcc aattcagtag gtgcattgga atcaagcctg      3180
gctacctgca tgctgttcct tttctttct  tcttttagcc attttgctaa gagacacagt      3240
cttctcatca cttcgtttct cctattttgt tttactagtt ttaagatcag agttcacttt      3300
ctttggactc tgcctatatt ttcttacctg aactttgca  agttttcagg taaacctcag      3360
ctcaggactg ctatttagct cctcttaaga agattaaaag agaaaaaaaa aggccctttt      3420
aaaaatagta tacacttatt ttaagtgaaa agcagagaat tttatttata gctaatttta      3480
gctatctgta accaagatgg atgcaaagag gctagtgcct cagagagaac tgtacggggt      3540
ttgtgactgg aaaaagttac gttcccattc taattaatgc cctttcttat ttaaaaacaa      3600
aaccaaatga tatctaagta gttctcagca ataataataa tgacgataat acttcttttc      3660
cacatctcat tgtcactgac atttaatggt actgtatatt acttaattta ttgaagatta      3720
ttatttatgt cttattagga cactatggtt ataaactgtg tttaagccta caatcattga      3780
tttttttttg ttatgtcaca atcagtatat cttctttggg gttacctctc tgaatattat      3840
gtaaacaatc caaagaaatg attgtattaa gatttgtgaa taaattttta gaaatctgat      3900
tggcatattg agatatttaa ggttgaatgt ttgtccttag gataggccta tgtgctagcc      3960
cacaaagaat attgtctcat tagcctgaat gtgccataag actgaccttt taaaatgttt      4020
tgagggatct gtggatgctt cgttaatttg ttcagccaca atttattgag aaaatattct      4080
gtgtcaagca ctgtgggttt taatatttt  aaatcaaacg ctgattacag ataatagtat      4140
ttatataaat aattgaaaaa aatttctctt tgggaagagg gagaaaatga aataaatatc      4200
attaaagata actcaggaga atcttcttta caattttacg tttagaatgt ttaaggttaa      4260
gaaagaaata gtcaatatgc ttgtataaaa cactgttcac tgttttttt  aaaaaaaaaa      4320 cttgatttgt tattaacatt gatctgctga caaaacctgg gaatttgggt tgtgtatgcg      4380
aatgtttcag tgcctcagac aaatgtgtat ttaacttatg taaaagataa gtctggaaat      4440
aaatgtctgt ttatttttgt actatttaaa aattgacaga tctttctga  agaaaaaaaa      4500 aaaaaaa                                                              4507
```

PHARMACEUTICAL COMPOSITION FOR TREATMENT OF EYE PAIN, CONTAINING PGE2 SYNTHESIS INHIBITOR

CROSS REFERENCE TO RELATED APPLICATIONS

This application is a national stage application under 35 U.S.C. 371 and claims the benefit of PCT Application No. PCT/KR2012/011631 having an international filing date of Dec. 27, 2012, which designated the U.S., which PCT application claimed the benefit of Korean Patent Application No. KR 10-2011-0146450 filed Dec. 29, 2011, and Korean Patent Application No. KR 10-2012-0074204 filed Jul. 6, 2012, the disclosures of each of which are incorporated herein by reference.

TECHNICAL FIELD

The present invention relates to a pharmaceutical composition for treating ocular pain, which contains a PGE2 synthesis inhibitor.

BACKGROUND ART

Dry eye syndrome is a very common disease reported to have a prevalence of 5.5-15% depending on study population, age and diagnosis standard, which are used in various epidemiological studies in the world. This disease is characterized by ocular pain, an irregular corneal surface, blurred and fluctuating vision, and increased risk of corneal ulcer. The change in corneal permeability caused by chronic dry eyes and keratitis sicca resulting from unstable tear film has been known to cause inflammations, which has been demonstrated by increased inflammation-mediated chemokine and cytokine in tears, increased immune activity and expression of adhesion molecules (HLA-DR and inter-cellular adhesion molecule 1 [ICAM-1]) by conjunctival epithelial cells, and increased T lymphocytes in the conjunctiva. Corneal ulcer resulting from keratoconjunctivitis sicca (KCS) may lead to poor vision, vision loss and, even blindness. It has been reported that the level and activity of matrix metalloproteinase-9 (MMP-9) greatly increase not only in the tears of patients with dry eye syndrome, but also in the corneal epithelium and tears of experimental dry eye (EDE) mice. Dry eye syndrome is a disorder of the tear film due to tear deficiency or changes in tear components, which is accompanied by various symptoms of ocular discomfort. Recently, the definition of dry eye syndrome has expanded, because as new types of dry eye syndromes with a neurogenic component (such as dry eyes that occur after LASIK procedures), ocular surface diseases due to an altered tear film composition, and the like have occurred (American Journal of Ophthalmology, 140. 507, 2005).

Dry eye syndrome is found in more than 50% of total patients visiting ophthalmic clinics, and the elderly, particularly 70 to 80% of post-menopausal women, suffer from ocular discomfort due to dry eye syndrome. In the past, it was considered that the pathological cause of dry eye syndrome was the aqueous layer deficiency resulting from decreased tear production by the lacrimal glands. However, in recent years, it has been found that the primary causes of dry eye syndrome are inflammatory responses to external stimuli, or endogenous inflammatory responses, which cause problems associated with chronic ocular surface damage arising from disorders of corneal epithelial cells, and decreased interactions between corneal epithelial cells and corneal keratocytes. Dry eye syndrome may be developed by various causes such as aging, hormonal changes, environmental factors (wind, heat, dust, cigarette smoke, hair dryers, etc.), a chronic low blink rate (VDT syndrome), contact lens wear, LASIK vision correction surgery, medications, and autoimmune diseases (lupus, rheumatoid arthritis and Sjogren's syndrome) (American Journal of Ophthalmology, 137, 337-342, 2004).

Meanwhile, NASAID, a non-specific COX enzyme inhibitor that is used to alleviate inflammation, has the effect of reducing prostaglandin levels in a non-specific manner. This drug is known to alleviate inflammation and pain, but is also known to produce inflammatory products such as leukotrienes, lipoxins, hydroperoxyeicosatetraenoic acids and the like. In the ophthalmic field, non-specific COX enzyme inhibitors have been developed and used as eye drops, but serious side effects such as corneal perforation, which are caused by the activation of the above inflammatory products, have been reported.

Accordingly, the present inventors have made extensive efforts to develop a pharmaceutical composition for treating or treating ocular diseases, including dry eye syndrome, which cause ocular pain. As a result, the present inventors have found that the expression level of prostaglandin E2 (PGE2) is higher in the tears of patients having an ocular pain symptom than in the tears of normal peoples and that when a PGE2 synthesis inhibitor is dropped into the eyes of animal models, it exhibits the effect of treating ocular pain, thereby completing the present invention.

DISCLOSURE

Technical Problem

It is an object of the present invention to provide a pharmaceutical composition for preventing or treating ocular pain, which contains a PGE2 synthesis inhibitor as an active ingredient, and a kit for diagnosing ocular pain, which can measure the level of PGE2.

Technical Solution

The present invention is based on the finding that the level of PGE2 in the tears of patients having an ocular pain symptom is high and the level of PGD2 in the tears is low. Based on this finding, the present invention provides a pharmaceutical composition for preventing or treating ocular pain, which contains a PGE2 synthesis inhibitor as an active ingredient, and a method for screening an ocular pain reliever that reduces the level of PGE2. In addition, the present invention may provide a kit that can diagnose ocular pain by measuring the levels of PGE2, PGD2 and COX2 in the tear of a patient, and also provide information for diagnosing ocular pain.

To achieve the above object, in one embodiment, the present invention provides a pharmaceutical composition for preventing or treating ocular pain, which contains a PGE2 synthesis inhibitor as an active ingredient.

In another embodiment, the present invention provides a health functional food for preventing or relieving ocular pain, which contains a PGE2 synthesis inhibitor as an active ingredient.

In the present invention, the PGE2 synthesis inhibitor may be selected from the group consisting of 15-deoxy-$\Delta^{12,14}$-PGJ$_2$, exisulind, NS-398, leukotriene C4, mk-886, analogues of MK-886, MF63, thienopyrrole, naphthalene disulphonamide, resveratrol and γ-hydroxybutenolide.

In the present invention, the pharmaceutical composition may be for reducing the expression level of PGE2.

In the present invention, the ocular pain is ocular pain resulting from dry eye syndrome, inflammatory ocular disease or the use of a contact lens.

In the present invention, the pharmaceutical composition may be in the form of a suspension, dust, powder, granules, a tablet, a sustained-release formulation, an injectable formulation, an ointment, an eye drop, a capsule, a contact lens cleaner, or a contact lens lubricant. Also, the pharmaceutical composition may be for human use.

In the present invention, the health functional food may be in the form of a capsule, a tablet, granules, powder or a beverage.

In still another embodiment, the present invention provides a method for screening an ocular pain reliever, the method comprising the steps of:

(a) bringing a sample to be analyzed into contact with cells including a PGE2 protein represented by SEQ ID NO: 1;

(b) measuring the amount or activity of the protein; and (c) determining that the sample is a substance that relieves ocular pain, when the amount or activity of the protein is measured to be down-regulated.

In still another embodiment, the present invention provides a method for screening an ocular pain reliever, the method comprising the steps of:

(a) bringing a sample to be analyzed into contact with cells including a gene that encodes a PGE2 protein represented by SEQ ID NO: 1;

(b) measuring the expression level of the gene; and (c) determining that the sample is a substance that relieves ocular pain, when the expression level of the gene is measured to be down-regulated, wherein the gene that encodes the PGE2 protein may be represented by SEQ ID NO: 2.

In still another embodiment, the present invention provides a method for screening an ocular pain reliever, the method comprising the steps of:

(a) bringing a sample to be analyzed into contact with cells including a COX2 protein represented by SEQ ID NO: 3;

(b) measuring the amount or activity of the protein; and (c) determining that the sample is a substance that relieves ocular pain, when the amount or activity of the protein is measured to be down-regulated.

In still another embodiment, the present invention provides a method for screening an ocular pain reliever, the method comprising the steps of:

(a) bringing a sample to be analyzed into contact with cells including a gene that encodes a COX2 protein represented by SEQ ID NO: 3;

(b) measuring the expression level of the gene; and (c) determining that the sample is a substance that relieves ocular pain, when the expression level of the gene is measured to be down-regulated, wherein the gene that encodes the COX2 protein may be represented by SEQ ID NO: 4.

In still another embodiment, the present invention provides a pharmaceutical composition for preventing or treating ocular pain, which contains a COX2 inhibitor as an active ingredient.

In still another embodiment, the present invention provides a method for providing information for diagnosis of ocular pain, the method comprising the steps of:

(a) measuring the level of PGE2, represented by SEQ ID NO: 1, in a biological sample isolated from a patient; and (b) comparing the level of PGE2 with that in a normal control sample.

In the present invention, the method for providing information may further comprise a step of measuring the level of PGD2 or COX2 and comparing the measured level with that in the normal control sample. Herein, when the levels of PGE2 and COX2 are higher than those in the normal control sample and the level of PGD2 is lower than that in the normal control sample, the patient may be determined to have ocular pain.

In another embodiment, the present invention provides a kit for diagnosing or predicting ocular pain, which comprises an antibody that binds specifically to a protein attached to PGE2.

In the present invention, the kit for diagnosing or predicting ocular pain may further comprise an antibody that binds specifically to a protein attached to PGD2 or a protein attached to COX2.

The kit may comprise antibodies that bind specifically to proteins attached to PGE2, PGD2 and COX2. The attached proteins may be horseradish peroxidase, alkaline phosphatase or β-galactosidase.

In the present invention, the levels of PGE2, PGD2 and COX2 may be measured by enzyme-linked immunosorbent assay (ELISA), radioimmunoassay (RIA), gas chromatography mass-spectroscopy (GC-MS), liquid chromatography mass-spectroscopy (LC-MS) or LC-MS/MS.

The composition of the present invention may be prepared as a neutraceutical composition or a food composition.

When the composition of the present invention is prepared as a pharmaceutical composition, it contains a pharmaceutically acceptable carrier. Examples of the pharmaceutically acceptable carrier that is contained in the pharmaceutical composition of the present invention include, but are not limited to, lactose, dextrose, sucrose, sorbitol, mannitol, starch, acacia gum, calcium phosphate, alginate, gelatin, calcium silicate, microcrystalline cellulose, polyvinyl pyrrolidone, cellulose, water, syrup, methyl cellulose, methyl hydroxybenzoate, propyl hydroxybenzoate, talc, magnesium stearate and mineral oil, which are commonly used in the preparation of pharmaceutical compositions. The pharmaceutical composition of the present invention may further contain, in addition to the above-described components, a lubricant, a wetting agent, a sweetener, a flavoring agent, an emulsifier, a suspending agent, a preservative, or the like. Suitable pharmaceutically acceptable carriers and formulations are described in detail in Remington's Pharmaceutical Sciences (19$^{th}$ ed., 1995).

The pharmaceutical composition of the present invention may be administered orally or parenterally. For parenteral administration, the composition may be administered intravenously, subcutaneously, intramuscularly, intraperitoneally, transdermally, intramucosally or intraocularly.

The suitable dose of the pharmaceutical composition of the present invention may vary depending on various factors such as a method for formulation thereof, a method for administration thereof, the patient's age, weight, sex or disease condition, diet, the time of administration, the route of administration, elimination rate and response sensitivity. The dose of the pharmaceutical composition of the present invention may preferably be 0.001-100 mg/kg (body weight)/day for an adult, more preferably 0.01-80 mg/kg (body weight)/day, and most preferably 0.1-60 mg/kg (body weight)/day. Also, under the discretion of the physician or pharmacist, it may be administered once or several times per day. Particularly, for intraocular administration, about 0.001-3% (w/v), and preferably about 0.01-1% (w/v), of the formulation is administered intraocularly once or several times per day.

The pharmaceutical composition or health functional food of the present invention may be prepared in single-dose forms or in multi-dose packages using a pharmaceutically acceptable carrier and/or excipient according to a method that may be easily carried out by those skilled in the art.

According to an embodiment of the present invention, a formulation of the composition of the present invention may be solution, suspension, syrup, emulsion, liposome, extract, dust, powder, granule, tablet, sustained-release formulation, eye drop, capsule, contact lens cleaner or contact lens lubricant, and may further comprise a dispersant or a stabilizer.

As used herein, the term "diagnosing" refers to identifying the presence or features of a pathological condition, and is intended to include determination of the susceptibility of a subject to a specific disease or disorder, determination of whether a subject has a specific disease or disorder, and determination of prognosis of a subject having a specific disease or disorder.

The term "sample" as used with reference to the method for screening herein means an unknown candidate that is used in screening to examine whether it influences the expression level of a gene or the amount or activity of a protein. Examples of the sample include, but are not limited to, chemical substances, nucleotides, antisense-RNA, and natural extracts.

The measurement of a change in the expression level of a gene may be carried out according to various methods known in the art. For example, it may be carried out using RT-PCR (Sambrook et al., Molecular Cloning. A Laboratory Manual, $3^{rd}$ ed. Cold Spring Harbor Press (2001)), Northern blotting (Peter B. Kaufma et al., Molecular and Cellular Methods in Biology and Medicine, 102-108, CRC press), cDNA microarray hybridization (Sambrook et al., Molecular Cloning. A Laboratory Manual, $3^{rd}$ ed. Cold Spring Harbor Press (2001)) or in situ hybridization (Sambrook et al., Molecular Cloning. A Laboratory Manual, $3^{rd}$ ed. Cold Spring Harbor Press (2001)).

When the measurement is carried out according to the RT-PCR protocol, total RNA is extracted from cells treated with the sample, and single-stranded cDNA is prepared from the total RNA using oligo dT primer and reverse transcriptase. Then, a PCR reaction is performed using the single-stranded cDNA as a template and a gene-specific primer set. The gene-specific primer set is shown in Table 2 below. The PCR amplification product is electrophoresed, and the resulting bands are analyzed to determine a change in the expression level of the gene.

The measurement of a change in the amount of protein can be carried out according to various immunoassay methods known in the art. Examples of the immunoassay methods include, but are not limited to, radioimmunoassay, radioimmunoprecipitation, immunoprecipitation, enzyme-linked immunosorbent assay (ELISA), capture-ELISA, inhibition or competition assay, and sandwich assay. The immunoassay or immunostaining method is described in Enzyme Immunoassay, E. T. Maggio, ed., CRC Press, Boca Raton, Florida, 1980; Gaastra, W., Enzyme-linked immunosorbent assay (ELISA), in Methods in Molecular Biology, Vol. 1, Walker, J. M. ed., Humana Press, NJ, 1984; and Ed Harlow and David Lane, Using Antibodies, A Laboratory Manual, Cold Spring Harbor Laboratory Press, 1999. For example, when the method of the present invention is carried out according to the radioimmunoassay method, protein-specific antibodies labeled with radioisotopes (e.g., $C^{14}$, $I^{125}$, $P^{32}$ and $S^{35}$) may be used. When the method of the present invention is carried out by the ELISA assay, a specific embodiment of the present invention includes the steps of: (a) coating an extract from sample-treated cells on the surface of a solid substrate; (b) allowing the cell extract to react with a protein-specific antibody; (c) allowing the material resulting from step (b) to react with an enzyme-conjugated secondary antibody; and (d) measuring the activity of the enzyme. The solid substrate is preferably a hydrocarbon polymer (e.g., polystyrene or polypropylene), glass, a metal or gel, and most preferably a microtiter plate. The enzyme conjugated to the secondary antibody includes, but is not limited to, an enzyme that catalyzes a color-development reaction, a fluorescent reaction, a luminescent reaction or an infrared reaction. Examples of the enzyme include alkaline phosphatase, β-galactosidase, horseradish peroxidase, luciferase and cytochrome P450. When alkaline phosphatase is used as the enzyme conjugated to the secondary antibody, the substrate used may be a color-development substrate, such as alkaline phosphatase, bromochloroindolylphosphate (BCIP), nitro blue tetrazolium (NBT), naphthol-As-B1-phosphate or ECF (enhanced chemifluorescence). When horseradish peroxidase is used as the enzyme, the substrate used may be chloronaphthol, aminoethylcarbazol, diaminobenzidine, D-luciferin, lucigenin (bis-N-methylacridinium nitrate), resorufin benzyl ether, luminol, Amplex Red reagent (10-acetyl-3,7-dihydroxyphenoxazine), TMB (3,3,5,5-tetramethylbenzidine), ABTS (2,2'-azine-di[3-ethylbenzthiazoline sulfonate]), or o-phenyldiamine (OPD). In the ELISA assay, the measurement of the final enzymatic activity or signal can be carried out according to various methods known in the art. If biotin is used as the label, the signal can be easily detected with streptavidin, and if luciferase is used as the label, the signal can be easily detected with luciferin.

For use in the diagnostic kit, PGE2, PGD2 and COX2 are preferably detachably labeled. A variety of techniques available for labeling biomolecules are well known to those skilled in the art and are considered to be within the scope of the present invention. Such techniques are described in Tijssen, Practice and theory of enzyme immuno assays', Burden, RH and von Knippenburg (Eds), Volume 15 (1985), 'Basic methods in molecular biology'; Davis L G, Dibmer M D; Battey Elsevier (1990), Mayer et al., (Eds) 'Immunochemical methods in cell and molecular biology' Academic Press, London (1987), or in the series 'Methods in Enzymology', Academic Press, Inc.

There are many different labels and methods of labeling known to those of ordinary skill in the art. Examples of labels that may be used in the present invention include enzyme, radioactive isotopes, colloidal metals, fluorescent compounds, chemiluminescent compounds, and bioluminescent compounds.

Labels that are commonly used include, but are not limited to, fluorochromes (e.g., fluorescein, rhodamine, Texas Red, etc.), enzymes (e.g., horse radish peroxidase, β-galactosidase, alkaline phosphatase), radioactive isotopes (e.g., $^{32}P$ or $^{125}I$, biotin, digoxygenin, colloidal metals, chemi- or bioluminescent compounds (e.g., dioxetanes, luminol or acridiniums) Labeling procedures, such as covalent coupling of enzymes or biotinyl groups, iodinations, phosphorylations, etc., are well known in the art.

Detection methods include, but are not limited to, autoradiography, fluorescence microscopy, direct and indirect enzymatic reactions, etc. Detection assays that are commonly used include radioisotopic or non-radioisotopic methods. These assays include, inter alia, RIA (Radioimmuno Assay) and IRMA (Immune Radioimmunometric Assay), EIA (Enzyme Immuno Assay), ELISA (Enzyme Linked Immuno Sorbent Assay), FIA (Fluorescent Immuno Assay) and CLIA(Chemioluminescent Immune Assay).

Advantageous Effects

When the inventive pharmaceutical composition for preventing or treating ocular disease, which contains a PGE2 synthesis inhibitor as an active ingredient, is used, it can selectively inhibit the expression level of PGE2, thereby alleviating an ocular pain symptom and exhibiting the effects of preventing and treating dry eye syndrome. In addition, when the kit for measuring the amounts of PGE2, PGD2 and COX2 is used, it can easily diagnose ocular pain in clinical practice, Thus, the kit can be widely used to examine the state of not only dry eye syndrome patients but also patients following ocular surgery.

MODE FOR INVENTION

Hereinafter, the present invention will be described in detail with reference to examples. It is to be understood, however, that these examples are for illustrative purposes and are not intended to limit the scope of the present invention.

Example 1

Analysis of components in tears of ocular pain patients

The tears of 23 patients showing a non-Sjogren type ocular pain symptom and 17 normal persons were collected using polyester fiber rods (TRANSORB® WICKS, FILTRONA, Richmond, Va.), and the levels of prostaglandin in the collected tears were measured by nano-liquid chromatography tandem mass spectrometry (LC-MS/MS) using an Applied Biosystem/MDS Sciex 4000 Qtrap quadrupole mass spectrometer (AB/MDS Sciex, Concord, Canada).

As a result, it was shown that the level of PGE2 in the tears of the patient group showing the ocular pain symptom was at least three times higher than that in the tears of the normal persons and that the level of PGD2 in the tears of the patient group was 7% of the level of PGD2 in the tears of the normal persons (Table 1).

TABLE 1

|  | Dry eye patients (n = 46) | Control group (n = 33) | p value |
| --- | --- | --- | --- |
| PGE2 (ng/ml) | 136.25 ± 170.82 | 43.89 ± 41.83 | 0.003** |
| PGD2 (ng/ml) | 5.41 ± 11.00 | 72.15 ± 202.42 | 0.028* |

Example 2

Measurement of ocular pain symptom severity as a function of PGE2 level

Before tears were collected from the patient group showing the ocular pain symptom and the normal group, the severity of the symptom was measured by the visual analogue scale. The visual analogue scale ranged from 0 (no pain) to 10 (worst pain or discomfort). Whether the symptom severity is related to a change in the prostaglandin level was statistically analyzed.

Figure 1:
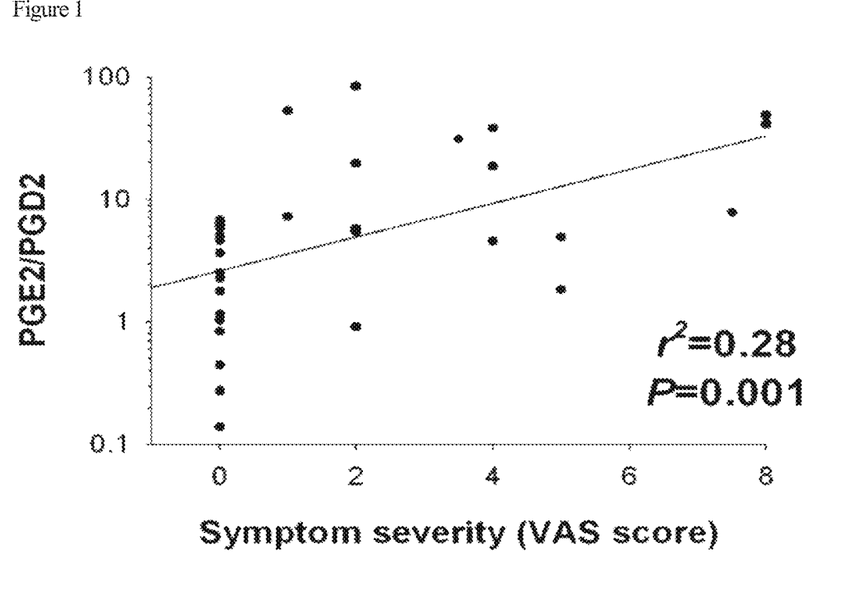
FIG. 1 is a graph showing the relationship between the level of PGE2/PGD2 in the tears of patients having an ocular pain symptom and the symptom severity of the patients.

As a result, it could be seen that, as the patient's discomfort caused by ocular pain increased, the PGE2/PGD2 ratio increased (FIG. 1).

Example 3

Experiment on ocular pain-induced mice

B6 mice were exposed to the environment in which ocular pain was induced using a dry eye chamber for 1 week. The exposed mice were divided into a test group and a control group, and then each of substances known as PGE synthesis inhibitors was administered intraocularly to each of the groups. To the test group, 5 μg/ml of celecoxib (Sigma) was administered intraocularly twice a day, and to the control group, 0.1% hyaluronic acid was administered intraocularly.

Figure 2:
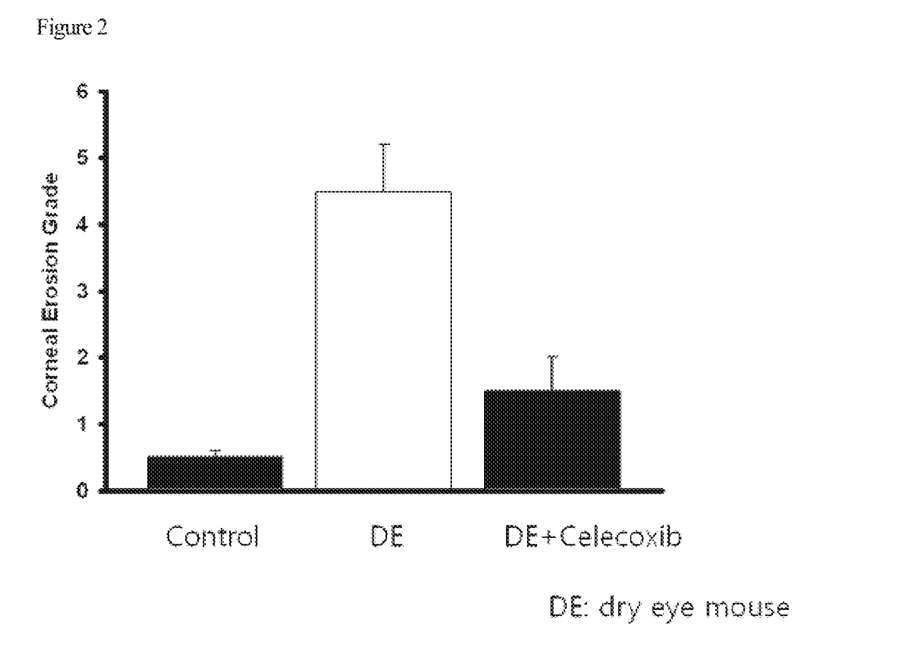
FIG. 2 shows the results of analyzing the degree of ocular discomfort after administering a COX2 inhibitor intraocularly to ocular pain-induced mice.

After 1 week of the intraocular administration, the corneal erosion of each of the test group and control group mice was measured using a standardized protocol. As a result, it could be seen that the corneal erosion of the test group administered intraocularly with celecoxib significantly decreased (FIG. 2).

Figure 3:
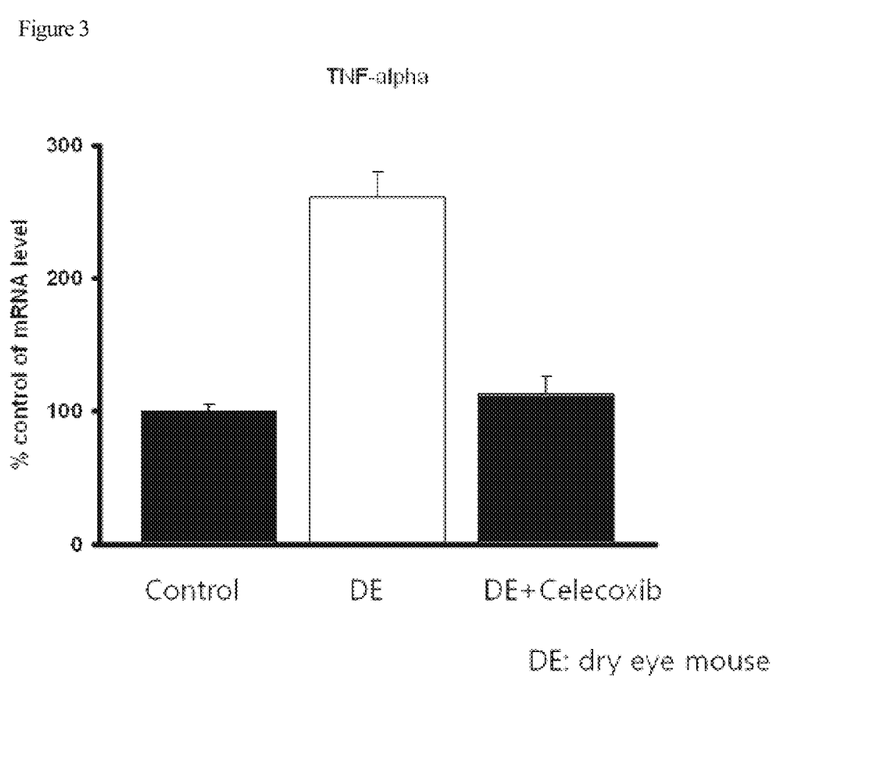
FIG. 3 shows the results of measuring the mRNA level of TNF-alpha after administering a COX2 inhibitor intraocularly to ocular pain-induced mice.
Figure 4:
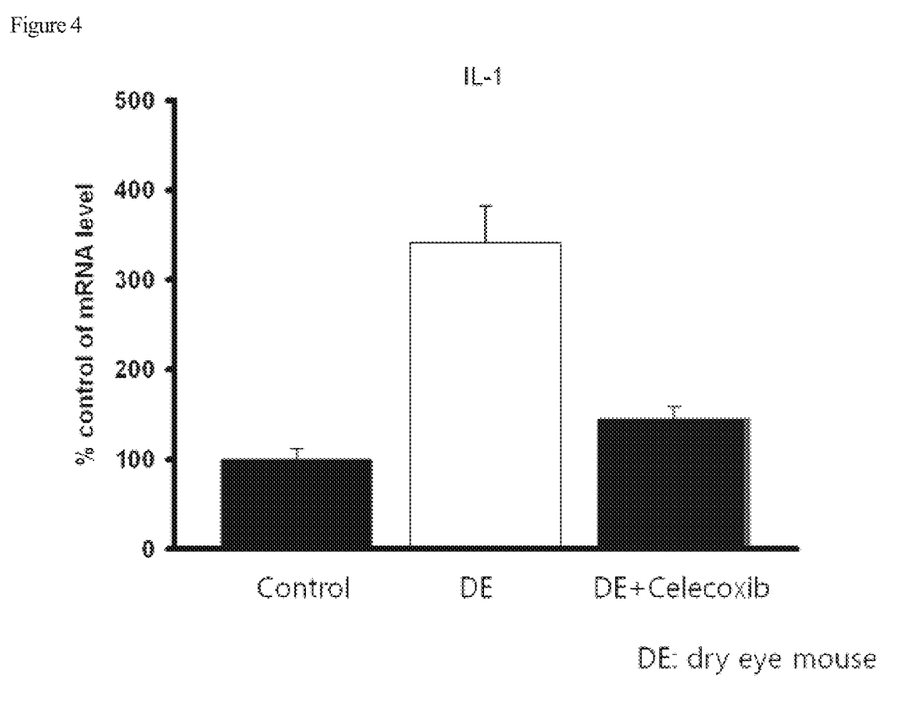
FIG. 4 shows the results of measuring the mRNA level of IL-1 after administering a COX2 inhibitor intraocularly to ocular pain-induced mice.

In addition, after 1 week of the intraocular administration, the eyeballs of the test group and control group mice were enucleated, and the mRNA levels of TNF-alpha and IL-1 on the surface of the enucleated eyeballs were measured by real time RT-PCR. As a result, it was shown that, in the case of the test group administered intraocularly with celecoxib, the mRNA levels of TNF-alpha and IL-1 greatly decreased (FIGS. 3 and 4).

Example 4

Experiment on administration of PEG2 synthesis inhibitors to eye pain patients

PGE2 synthesis inhibitors were administered intraocularly to patients having an ocular pain symptom, and whether the number of eye blinks of the patient group was reduced compared to that of a control group was examined. The PGE2 synthesis inhibitors used were 15-deoxy-$\Delta^{12,14}$-$PGJ_2$, exisulind, NS-398, leukotriene C4, mk-886, analogues of MK-886, MF63, thienopyrrole, naphthalene disulphonamide, resveratrol, and γ-hydroxybutenolide.

As a result, it was shown that, when the PGE synthesis inhibitors were administered intraocularly, they reduced ocular discomfort to thereby reduce the number of eye blinks (Table 2).

TABLE 2

| PGE2 synthesis inhibitors used | Number of eye blinks of treated group (n = 10) for 5 min | Number of eye blinks of control group (n = 10) for 5 min | P value |
| --- | --- | --- | --- |
| 15-deoxy-$\Delta^{12,14}$-PGJ$_2$ | 11 | 25 | 0.03* |
| Exisulind | 14 | 18 | 0.02* |
| NS-398 | 13 | 20 | 0.015* |
| Leukotriene C4 | 17 | 21 | 0.04* |
| mk-886 | 15 | 24 | 0.04* |
| Analogues of MK-886 | 10 | 27 | 0.012* |
| MF63 | 9 | 24 | 0.02* |
| Thienopyrrole | 13 | 23 | 0.005* |
| Naphthalene disulphonamide | 16 | 20 | 0.004* |
| Resveratrol | 17 | 19 | 0.04* |
| γ-hydroxybutenolide | 18 | 22 | 0.037* |

Example 5

Experiment on administration of selective COX2 inhibitors to ocular pain patients In order to examine whether selective COX2 inhibitors are effective in reducing an ocular pain symptom compared to non-selective COX2 inhibitors, each of selective COX2 inhibitors, non-selective COX2 inhibitors and NSAID was administered. Specifically, selective COX2 inhibitors were administered intraocularly to patients having an ocular pain symptom, and whether the number of eye blinks of the treated patients decreased compared to that of a control (Diclofenac) having non-selective COX2 inhibitory activity was examined. The selective COX2 inhibitors used were structurally classified, and Nimesulud, Celecoxib, Meloxicam, S-2474 (3,5-di-tert-buryl-4-hydroxybenzylidene), and cis-stilbenes were used as representatives of the classes. In addition, Ibuprofen was used as NSAID having selective COX2 inhibitory activity.

As a result, it could be seen that, when selective COX2 inhibitors were administered intraocularly, they reduced ocular discomfort to thereby reduce the number of eye blinks (Table 3).

TABLE 3

| Classes | Substances used | Number of eye blinks of treated group (n = 3) | Number of eye blinks of control group (n = 3) | P value |
| --- | --- | --- | --- | --- |
| Classic NSAIDs having selective COX2 inhibitory activity | Ibuprofen | 17 | 25 | 0.03 |
| Diary- or aryl-heteroaryl ether and thioether | Nimesulud | 16 | 22 | 0.04 |
| Vicinal diaryl heterocycle | Celecoxib | 17 | 23 | 0.012 |
| Structurally modified classic NSAIDs and other compounds | Meloxicam | 20 | 26 | 0.04 |
| Compounds having antioxidant activity | S-2474 | 15 | 27 | 0.004 |
| 1,2-diarylethylene derivatives | cis-Stilbenes | 22 | 29 | 0.03 |

Although the present disclosure has been described in detail with reference to the specific features, it will be apparent to those skilled in the art that this description is only of a preferred embodiment thereof, and does not limit the scope of the present invention. Thus, the substantial scope of the present invention will be defined by the appended claims and equivalents thereof

INDUSTRIAL APPLICABILITY

As described above, when the inventive pharmaceutical composition for preventing or treating ocular disease, which contains a PGE2 synthesis inhibitor as an active ingredient, is used, it can selectively inhibit the expression level of PGE2, thereby alleviating an ocular pain symptom and exhibiting the effects of preventing and treating dry eye syndrome.

SEQUENCE LIST TEXT

SEQ ID NOS: 1 and 2 represent the sequence of PGE2 protein and the sequence of a gene that encodes the protein, respectively, and SEQ ID NOS: 3 and 4 represent the sequence of COX2 protein and the sequence of a gene that encodes the protein, respectively.

The invention claimed is:

1. A method of preventing or treating ocular pain resulting from dry eye syndrome by administering a PGE2 synthesis inhibitor to a mammal having dry eye syndrome, wherein the PGE2 synthesis inhibitor is selected from the group consisting of 15-deoxy-$\Delta^{12,14}$-PGJ$_2$, Exisulind, Leukotriene C4, mk-886, Naphthalene disulphonamide, and γ-hydroxybutenolide.

2. A method of preventing or treating ocular pain resulting from dry eye syndrome by administering a COX2 inhibitor to a mammal having dry eye syndrome, wherein the COX2 synthesis inhibitor is selected from the group consisting of (E)-5-(3,5-di-ter-butyl-4-hydroxybenzylidene)-2-ethyl-1,2-isothiazolidine-1,1-dioxide, Meloxicam and cis-Stilbenes.

* * * * *

UNITED STATES PATENT AND TRADEMARK OFFICE
CERTIFICATE OF CORRECTION

| | |
|---|---|
| PATENT NO. | : 9,629,855 B2 |
| APPLICATION NO. | : 14/648970 |
| DATED | : April 25, 2017 |
| INVENTOR(S) | : Hyung Keun Lee and Jong Woo Shim |

It is certified that error appears in the above-identified patent and that said Letters Patent is hereby corrected as shown below:

In the Claims

In Claim 1, Column 20, Line 66, please delete "C4, mk-886, Naphthalene disulphonamide, and γ-hydroxy-" and insert --C4, mk-886, celecoxib, Thienopyrrole, Naphthalene disulphonamide, and γ-hydroxy- --

Signed and Sealed this
Thirtieth Day of May, 2017

Michelle K. Lee
*Director of the United States Patent and Trademark Office*